(12) United States Patent  (10) Patent No.: US 6,629,927 B1
Mesaros et al.  (45) Date of Patent: Oct. 7, 2003

(54) DIAGNOSTIC ULTRASOUND SYSTEM CART WITH INTEGRAL CABLE SUPPORTS

(75) Inventors: Robert Mesaros, Bothell, WA (US); Yas Matsui, Redmond, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/155,460

(22) Filed: May 23, 2002

(51) Int. Cl.[7] .................................................. A61B 8/00
(52) U.S. Cl. ........................................................ 600/437
(58) Field of Search ........................ 600/437; D24/185, D24/160; D14/100; 128/922; 211/151; D12/178; D8/303; 16/430, 429; 190/11

(56) References Cited

U.S. PATENT DOCUMENTS

| | | | |
|---|---|---|---|
| 4,625,731 A | | 12/1986 | Quedens et al. |
| 5,129,397 A | * | 7/1992 | Jingu et al. ................. 600/437 |
| 5,205,175 A | | 4/1993 | Garza et al. |
| D360,690 S | * | 7/1995 | Murakami ................. D24/160 |
| 5,505,203 A | * | 4/1996 | Deitrich et al. ............. 600/437 |
| 5,924,988 A | * | 7/1999 | Burris et al. ................ 600/437 |
| 6,142,940 A | | 11/2000 | Lathbury et al. |
| 6,447,451 B1 | * | 9/2002 | Wing et al. ................. 600/437 |

OTHER PUBLICATIONS

Philips, SONOS and HDI ultrasound system.*

* cited by examiner

Primary Examiner—Francis J. Jaworski
Assistant Examiner—Ruby Jain
(74) Attorney, Agent, or Firm—W. Brinton Yorks, Jr.

(57) ABSTRACT

A cart-borne ultrasound system has a control panel at the front of the cart for operating the ultrasound system and a handle at the front of the cart by which a user can push or pull the cart to a different location. The handle has an opening through which a probe cable can be slipped to hang the cable over the handle during transport, storage, or use. The handle also serves to raise and lower the system control panel. The handle can also be articulated to move it out of the way of a user in front of the control panel.

20 Claims, 6 Drawing Sheets

DIAGNOSTIC ULTRASOUND SYSTEM CART WITH INTEGRAL CABLE SUPPORTS

This invention relates to ultrasonic diagnostic imaging systems and, in particular, to ultrasound systems with integral probe cable supports.

Cart-borne ultrasound systems generally are capable of operating with a variety of ultrasound probes, each of which is specially designed for a particular exam or application. The systems usually have several connectors into which several probes can be connected at the same time. This enables the clinician to examine a patient with one probe and, if it is not found to produce the desired images, to pick up a second probe and begin examining the patient with it at the touch of a button.

Each probe, however, is connected to the system by a cable which can be three to six feet long or longer. Consequently the operator can spend a great deal of unproductive time managing these cables and keeping them from entangling each other. Moreover, cart-borne ultrasound systems are mounted on casters or wheels to enable them to be rolled to a lab or a patient's bedside. The probe cables can be a hazard to the operator and others if they become entangled in the wheels of the ultrasound system as it is being rolled from one location to another. Furthermore, when an ultrasound system cart rolls over a probe cable containing over a hundred tiny coaxial conductors, the cable can become damaged and the probe rendered inoperable. It is desirable for an ultrasound system to be designed to prevent these problems from occurring.

In accordance with the principles of the present invention, a cart-borne ultrasound system includes a handle by which the system can be adjusted or moved. The handle is discontinuous, enabling it to also be used to support probe cables. In the illustrated embodiments the handle is shown with an intermediate opening, with open ends, or with an opening on the side of the cart. In accordance with a further aspect of the present invention, the handle can articulate away from the position of the operator, thereby enabling the operator to more comfortably operate the ultrasound system.

Figure 1:
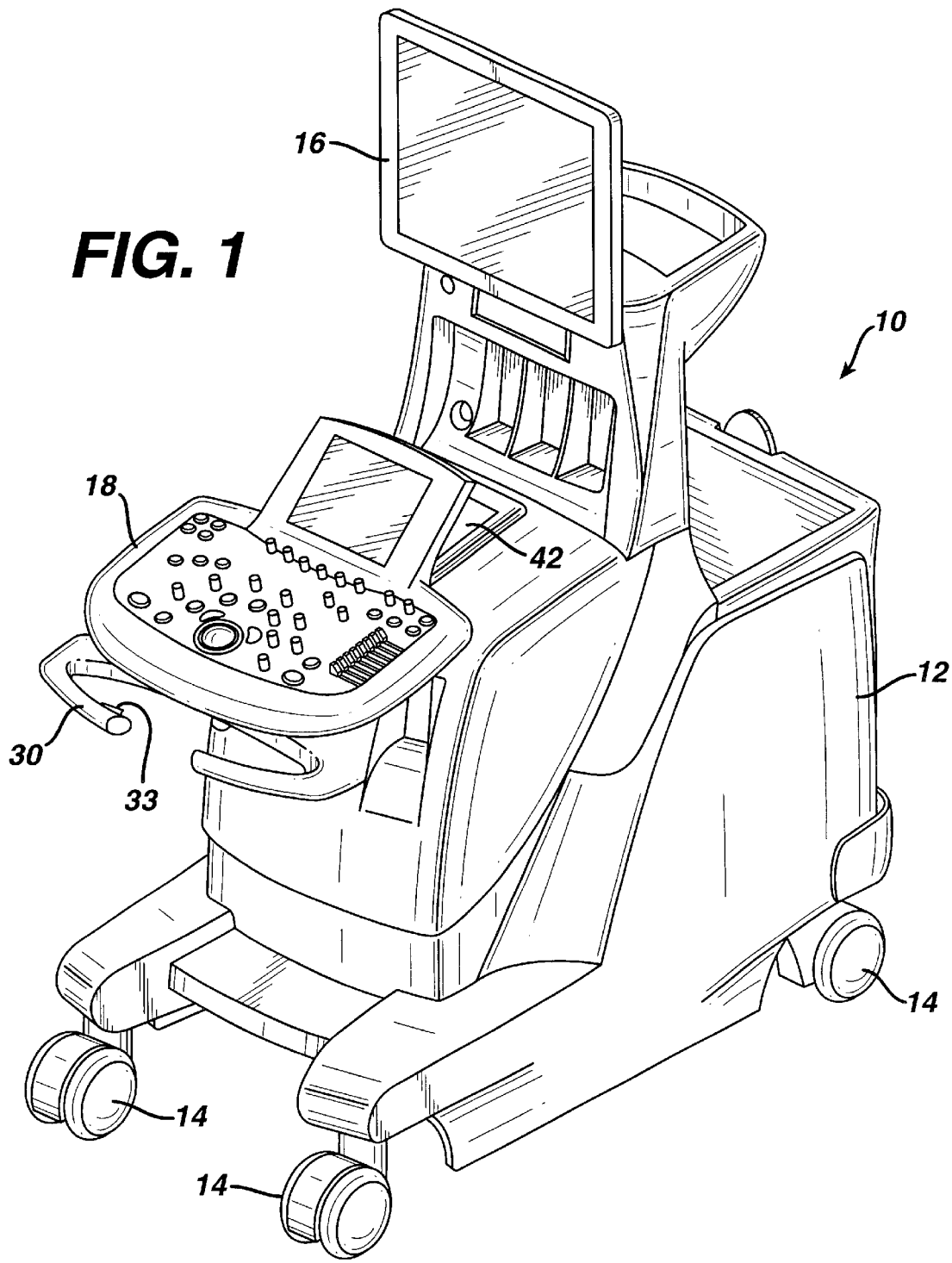
FIG. 1 illustrates a cart-borne ultrasound system in perspective.

Referring first to FIG. 1, a cart-borne ultrasound system 10 is shown in perspective. The cart includes an electronics bay 12 inside of which are located printed circuit boards for electronically processing received ultrasound signals. The ultrasound signals are processed to produce an image which is displayed on a display 16. The cart is mounted on wheels or casters 14 so that it can be rolled to a lab or a patient's bedside. In the front of the cart is a control panel 18 which contains a number of knobs, buttons, slide switches, and a trackball by which a user controls the ultrasound system. The control panel is mounted above a handle 30 which extends from the front of the ultrasound system. The handle 30 can be used to pull the cart to move it from one location to another. On the inside of the handle 30 is a handle lock release 33 which will be discussed below.

Figure 2:
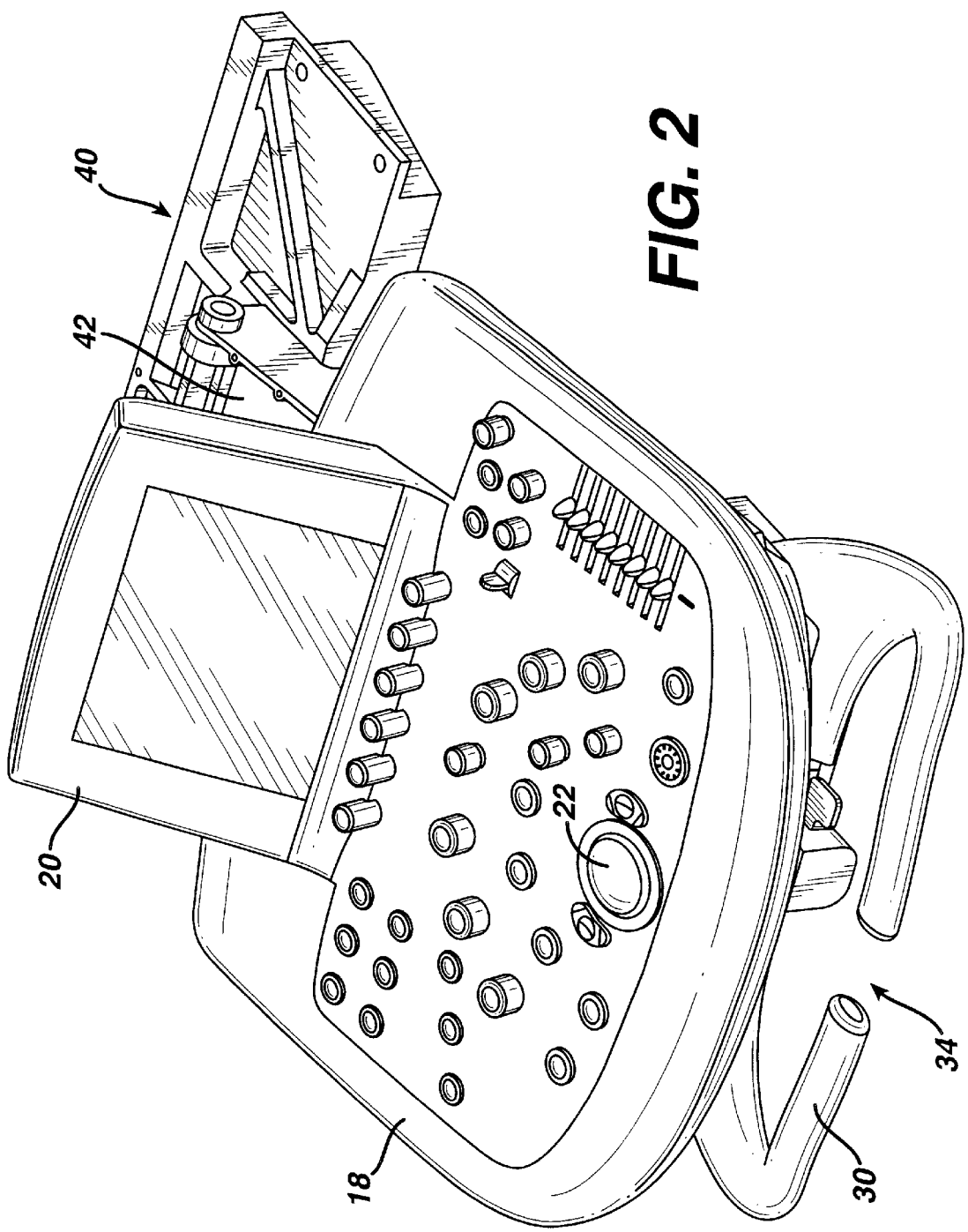
FIG. 2 illustrates the control panel and handle of the ultrasound system of FIG. 1 in greater detail.

The cart handle 30 and control panel 18 are shown in greater detail in FIG. 2. Prominent among the controls on the control panel 18 is a trackball 22, which is used to move cursors and selectors on the system user interface screen. At the back of the control panel is a touchscreen display 20 which presents selectable, programmable options for the user. Behind the control panel is an articulating control panel lift mechanism 40 which enables the control panel to be raised and lowered. The lift top 42 of this mechanism can be seen behind the control panel 18 in FIG. 1.

Located just below the control panel 18 is the cart handle 30. The cart handle in one embodiment is rigidly mounted to the lift mechanism 40. When so mounted the handle 30 can be used to raise and lower the lift mechanism and control panel to a height which is comfortable to the operator as more fully described in concurrently filed U.S. patent application Ser. No. 10/154,733 [ATL-294]. Since the handle is rigidly mounted to the lift mechanism which is mounted on the cart, the handle 30 can also be used to push and pull the cart to move it, and to otherwise manipulate the entire cart on its wheels.

Figure 3:
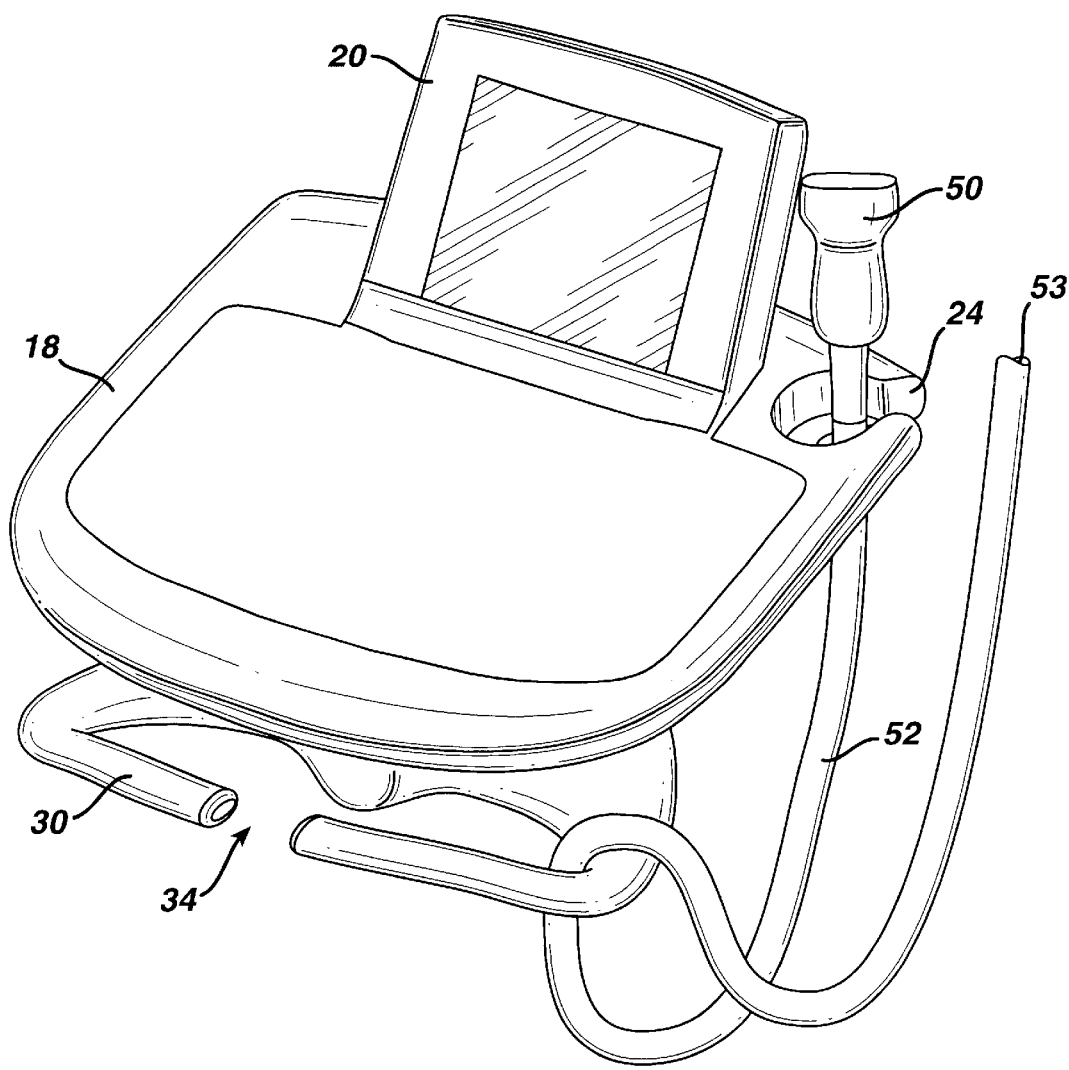
FIG. 3 illustrates an ultrasound system cart handle with a central opening in use as a cable support in accordance with a first embodiment of the present invention.

In accordance with a first embodiment of the present invention, the handle 30 is open in the middle 34 and closed at the lateral sides, rather than extending as a continuous section across the front of the cart. This opening permits the handle to serve yet another function, which is as a probe cable support as shown in FIG. 3. This drawing illustrates how the cable 52 of a probe 50 may be passed through the opening 34 and supported by the handle 30. This is very convenient for the user, as the handle/cable support is right in front of the control panel where the user is positioned to operate the ultrasound system. The distal end 53 of the probe cable terminates at a probe connector (not shown) which engages a mating probe connector on the ultrasound system cart. A preferred probe connector is shown in concurrently filed U.S. patent application Ser. No. 10/155,505 [ATL-297] which is incorporated herein by reference. That patent application shows a probe connector on the system mounted above the level of the control panel, keeping the connector end of the probe cable well above the floor. When the probe is placed in a probe holder 24 on the cart and the cable 52 hung from the handle 30, the entire cable is kept well above the wheels of the cart and presents no hazard to the Operator or other personnel.

Figure 4:
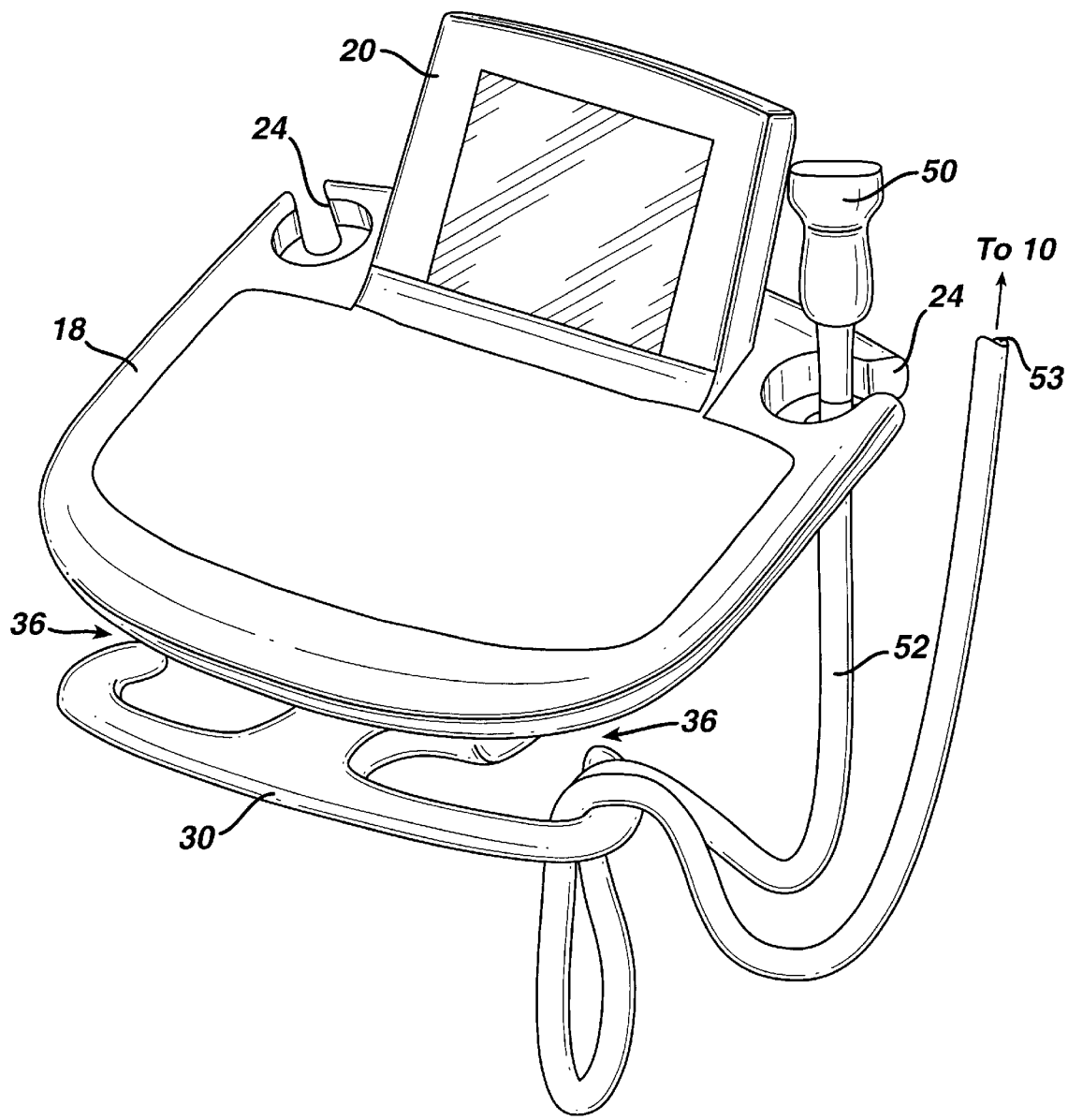
FIG. 4 illustrates an ultrasound system cart handle with open ends in use as a cable support in accordance with a second embodiment of the present invention.
Figure 5:
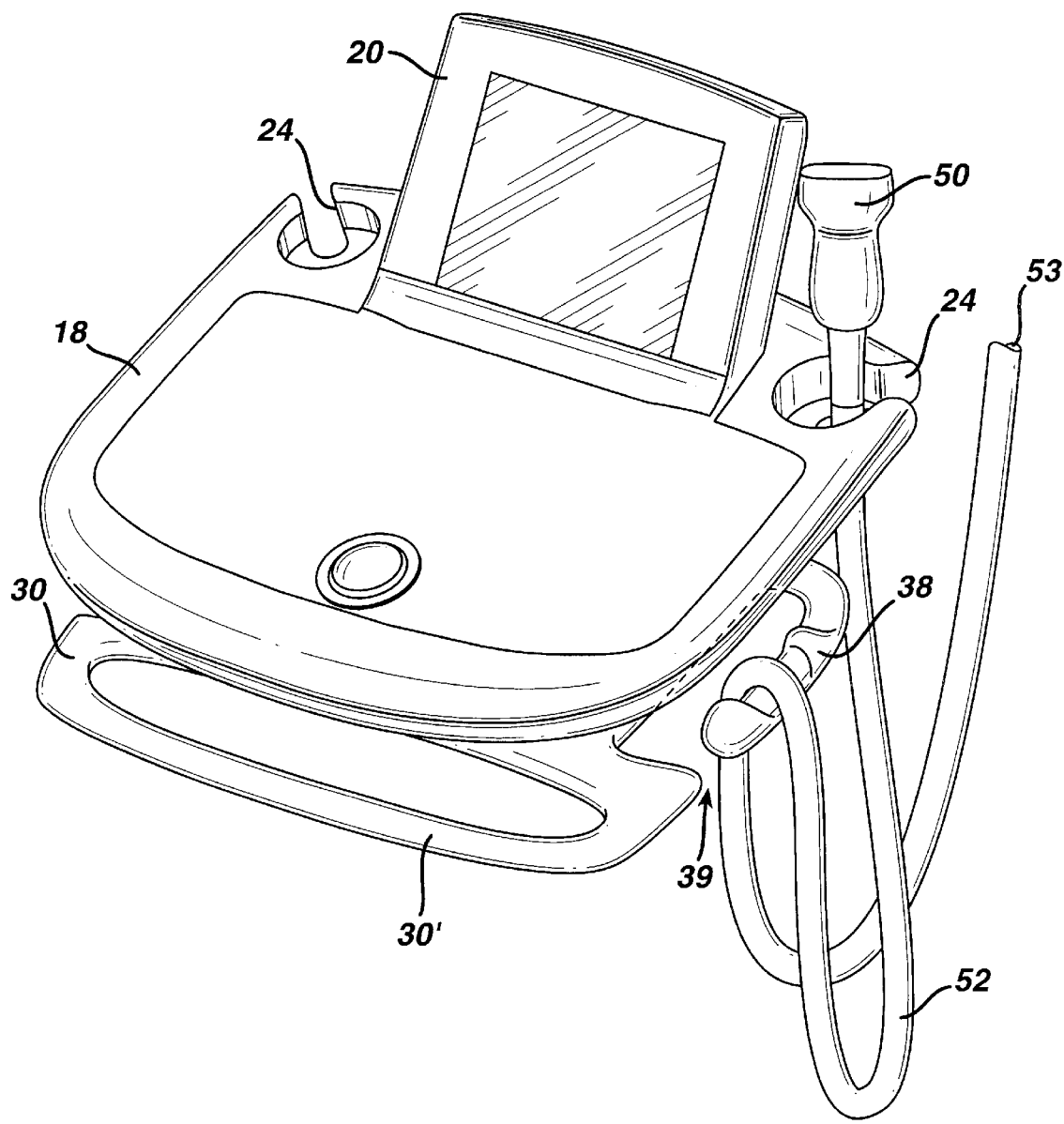
FIG. 5 illustrates an ultrasound system cart handle which is open on the side in use as a cable support in accordance with a third embodiment of the present invention.

FIG. 4 illustrates a second embodiment of the present invention, in which the handle 30 is closed in the center and open at the sides 36. In the illustrated embodiment the handle 30 is mounted to the cart at the center of the handle. As the drawing 35 shows, the cable 52 is easily slipped over the hooked handle end by way of the opening 36 at the end of the handle. This embodiment is also convenient for the operator to use, and similarly supports the cable to keep it well away from the floor and cart wheels.

Figure 6:
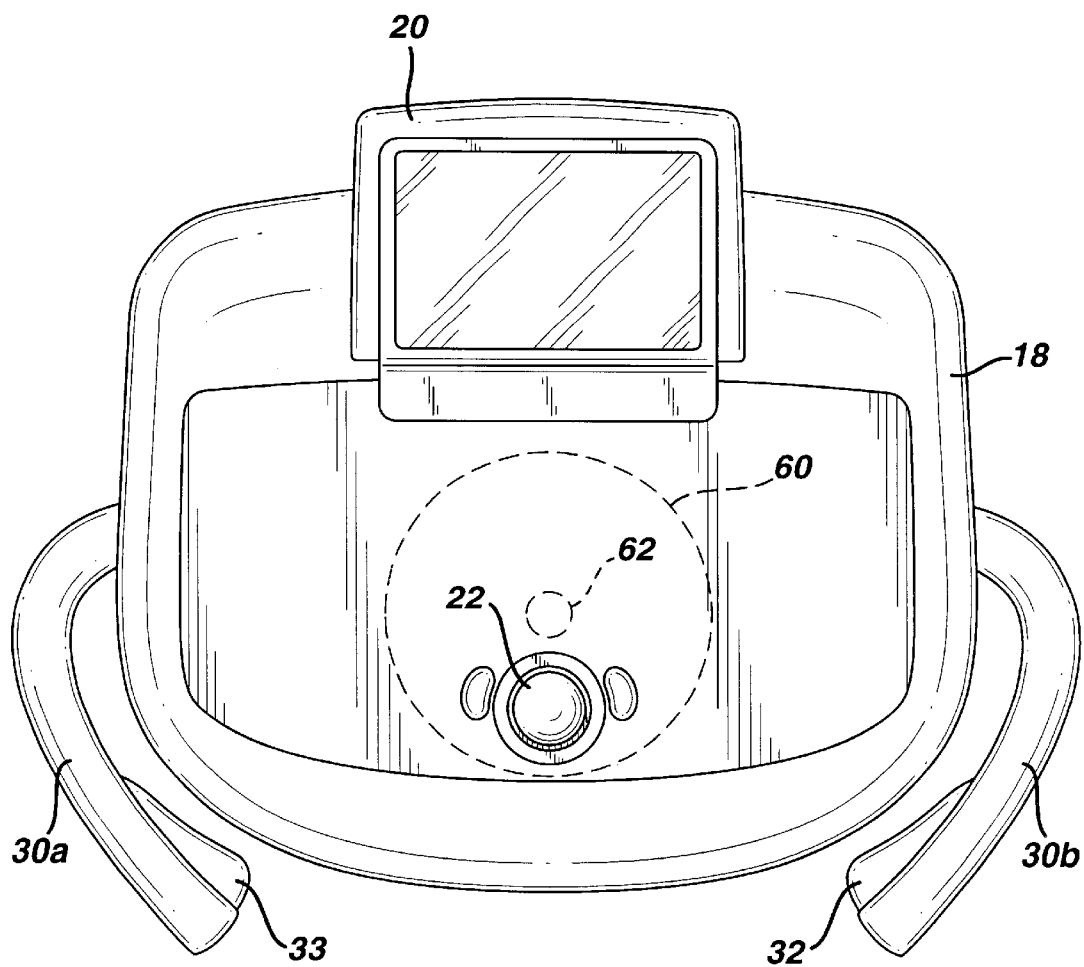
FIG. 6 illustrates an articulating ultrasound cart handle in accordance with a further aspect of the present invention.

In the embodiment shown in FIGS. 1 and 2 the handle 30 is seen to be located below the control panel and extends forward beyond the front of the control panel. As discussed above the handle 30 has several uses. It may be used to push or pull the mobile ultrasound cart. The handle can also be used to raise or. lower the control panel elevation when the lift release button 32 in the handle is depressed. The lift mechanism is normally locked in its current position and can only be raised or lowered when the lift release button 32, shown in FIG. 6, is depressed. This approach provides a rigid mechanism when the handle is used to move the cart. The handle may also be used to swivel the control panel on a swivel plate 60 or to move it laterally as described in concurrently filed U.S. patent application Ser. Nos. 10/155,529 and 10/155,459 [ATL-295 and ATL-296], although this may also be done by grasping the sides of the control panel to move it. In some operating situations, however, it may be that the handle is inconveniently located for comfortable scanning and system operation. For instance, when the control panel is lowered over the lap of an operator who is sitting, the handle may interfere with the legs of the operator or may prevent the operator from being as close to the front of the control panel as desired. In accordance with another aspect of the present invention, the handle may be moved out of the way as shown in FIG. 6. The handle lock release 33 is depressed to allow the handle 30 to split into two halves 30a and 30b, which can then be pivoted to the sides of the control panel as shown in the drawing. In this position the handle does not impede the operator during scanning. When scanning is completed and the handle is to be used to pull the cart-borne ultrasound system to a new location, the handle halves are swung back to their original center positions where they lock into place. The handle 30 is then rigidly positioned for pulling the cart or raising or lowering the control panel. In other embodiments unlocking the handle can permit the entire handle to swing or slide to one side of the control panel, in which case the handle can be fabricated as a single unit rather than separate halves.

In the embodiment shown in FIGS. 1 and 2 the handle 30 is seen to be located below the control panel and extends forward beyond the front of the control panel. As discussed above, the handle 30 has several uses. It may be used to push or pull the mobile ultrasound cart. The handle can also be used to raise or lower the control panel elevation when the lift release button 32 in the handle is depressed. The lift mechanism is normally locked in its current position and can only be raised or lowered when the lift release button 32, shown in FIG. 6, is depressed. This approach provides a rigid mechanism when the handle is used to move the cart. The handle may also be used to swivel the control panel on a swivel plate 60 or to move it laterally as described in concurrently filed U.S. patent [application Ser. No. ATL-295 and ATL-296], although this may also be done by grasping the sides of the control panel to move it. In some operating situations, however, it may be that the handle is inconveniently located for comfortable scanning and system operation. For instance, when the control panel is lowered over the lap of an operator who is sitting, the handle may interfere with the legs of the operator or may prevent the operator from being as close to the front of the control panel as desired. In accordance with another aspect of the present invention, the handle may be moved out of the way as shown in FIG. 6. The handle lock release 33 is depressed to allow the handle 30 to split into two halves 30a and 30b, which can then be pivoted to the sides of the control panel as shown in the drawing. In this position the handle does not impede the operator during scanning. When scanning is completed and the handle is to be used to pull the cart-borne ultrasound system to a new location, the handle halves are swung back to their original center positions where they lock into place. The handle 30 is then rigidly positioned for pulling the cart or raising or lowering the control panel. In other embodiments unlocking the handle can permit the entire handle to swing or slide to one side of the control panel, in which case the handle can be fabricated as a single unit rather than separate halves.

What is claimed is:

1. An ultrasound system including electronic circuitry which processes ultrasound signals for the formation of ultrasound images, an ultrasonic probe having a cable which connects to the electronic circuitry, and a display coupled to the circuitry for the display of ultrasound images, comprising:
    an elongated handle connected to the ultrasound system, the elongated handle ending in a terminus defining an opening through which a probe cable may vertically pass to support the probe cable with the handle, the handle being adapted to be gripped by an operator along a direction of elongation.

2. An ultrasound system including electronic circuitry which processes ultrasound signals for the formation of ultrasound images, an ultrasonic probe having a cable which connects to the electronic circuitry, and a display coupled to the circuitry for the display of ultrasound images, comprising:
    an elongated handle connected to the ultrasound system, the elongated handle ending in a terminus defining an opening through which a probe cable may vertically pass to support the probe cable with the handle, the handle being adapted to be gripped by an operator along a direction of elongation,
    wherein the handle includes ends extending laterally toward opposite sides of the ultrasound system and wherein the opening is in an intermediate location between the ends.

3. The ultrasound system of claim 2, wherein the handle has a center relative to its later sides; and wherein the opening is in the center of the handle.

4. An ultrasound system including electronic circuitry which processes ultrasound signals for the formation of ultrasound images, an ultrasonic probe having a cable which connects to the electronic circuitry, and a display coupled to the circuitry for the display of ultrasound images, comprising:
    an elongated handle connected to the ultrasound system, the elongated handle ending in a terminus defining an opening through which a probe cable may vertically pass to support the probe cable with the handle, the handle being adapted to be gripped by an operator along a direction of elongation,
    wherein the handle includes ends extending laterally toward opposite sides of the ultrasound system and wherein the opening is at a first side of the ultrasound system proximate to an end.

5. The ultrasound system of claim 4, wherein the opening is at the terminus of a hooked end of the handle.

6. The ultrasound system of claim 4, wherein the handle further includes a second opening at a second side of the ultrasound system proximate to a second end.

7. The ultrasound system of claim 4, wherein the handle has a center relative to its lateral sides; and wherein the handle is connected to the ultrasound system at the center of the handle.

8. The ultrasound system of claim 1, wherein the handle includes ends extending laterally toward and around opposite sides of the ultrasound system and wherein the opening through which a probe cable may vertically pass is located on one of the sides of the ultrasound system.

9. The ultrasound system of claim 8, wherein the opening defines a side handle which is open at one end.

10. The ultrasound system of claim 9, wherein the section of the handle which is in the front of the ultrasound system is a closed handle.

11. The ultrasound system of claim 2, 4, or 8, wherein the ultrasound system further comprises a mobile cart on which the electronics and display are mounted, the mobile cart having a front side, and wherein the handle is located on the front of the cart.

12. The ultrasound system of claim 11, wherein the handle further comprises means for moving the mobile cart.

13. The ultrasound system of claim 11, further comprising a control panel located at the front of the cart, wherein the handle further comprises means for articulating the control panel.

14. The ultrasound system of claim 13, wherein the control panel may be adjustably elevated, and wherein the handle further comprises means for changing the elevation of the control panel.

15. A cart-borne ultrasound system including a movable cart having a forward direction which opposes an operator position; electronic circuitry located on the cart which processes ultrasound signals for the formation of ultrasound images; and a display coupled to the circuitry for the display of ultrasound images, comprising:

a control panel coupled to the electronic circuitry for user control of the ultrasound system; and a handle located in front of the control panel, the handle being movable to a location which is not in front of the center of the control panel.

16. The cart-borne ultrasound system of claim 15, wherein the handle has a locked position in front of the control panel.

17. The cart-borne ultrasound system of claim 16, wherein the handle includes a control which releases the handle from its locked position.

18. The cart-borne ultrasound system of claim 16, wherein the handle comprises first and second handle halves which may be locked in front of the control panel or unlocked to move away from the front center of the control panel.

19. The cart-borne ultrasound system of claim 18, wherein the handle halves are pivotally mounted to swing to the sides of the control panel when the handle is unlocked.

20. A cart-borne ultrasound system comprising:

a mobile cart having a front side;

electronic circuitry located on the cart which processes ultrasound signals for the formation of ultrasound images;

a display coupled to the circuitry for the display of ultrasound images;

a control panel having a given elevation relative to the cart and located at the front side of the cart;

a probe connector located on the cart above the level of the control panel, the electronic circuitry, the display, the control panel and the probe connector being located on the cart at all times during use of the ultrasound system; and an elongated handle ending in a terminus defining an opening through which a probe cable may vertically pass to support the probe cable with the handle, the handle being adapted to be gripped by an operator along a direction of elongation, wherein the handle is located proximate to the control panel.

* * * * *